United States Patent [19]
Kawamura et al.

[11] Patent Number: 5,726,735
[45] Date of Patent: Mar. 10, 1998

[54] MEASUREMENT DEVICE WITH POLARIZING FILTER FOR NOISE ELIMINATION

[75] Inventors: Masunori Kawamura, Nagoya-shi; Setsuo Saitou, Aichi-gun, both of Japan

[73] Assignee: Nidek Co., Ltd., Japan

[21] Appl. No.: 595,826

[22] Filed: Feb. 2, 1996

[30] Foreign Application Priority Data

Feb. 2, 1995 [JP] Japan .................................. 7-039282

[51] Int. Cl.$^6$ .................................................. A61B 3/10
[52] U.S. Cl. ........................................ 351/215; 351/205
[58] Field of Search ............................ 351/205, 206, 351/212, 215, 221, 213, 211

[56] References Cited

FOREIGN PATENT DOCUMENTS 292216  11/1988  European Pat. Off. ............ 351/215

*Primary Examiner*—Huy Mai
*Attorney, Agent, or Firm*—Rossi & Associates

[57] ABSTRACT

An ophthalmic measuring apparatus for eliminating the noise ingredient of the light without eliminating the scattered light by molecules in crystalline lens of the examiner, to achieve stable results of measurements, the ophthalmic measuring apparatus provided a laser beam irradiating optical system for emitting and converging a laser beam to an eye, and a scattered light detecting optical system for detecting a light scattered by molecules in a crystalline lens from the laser beam, and also provided measuring device for measuring a composition in the crystalline lens on the basis of the intensity of the light detected by the scattered light detecting optical system, of which a first polarizing filter is disposed in the scattered light detecting optical system so as to be consistent with the polarizing axis of the laser beam of the laser beam irradiating optical system.

12 Claims, 1 Drawing Sheet

MEASUREMENT DEVICE WITH POLARIZING FILTER FOR NOISE ELIMINATION

BACKGROUND OF THE INVENTION

1. Field of the Invention

The present invention relates to an ophthalmic measuring apparatus, and more particularly to an ophthalmic measuring apparatus for irradiating and converging a laser beam to the eyeball of an eye, and guiding the light beam scattered by molecules in the crystalline lens through a light-receiving optical system to a photoelectric transducer, in order to measure the condition of a crystalline lens in accordance with the output signals of the photoelectric transducer.

2. Description of Related Art

There have been proposed an apparatus for measuring such as radii of particles within the crystalline lens by emitting and converging a laser beam to the eyeball of an eye, by guiding the scattered light scattered by molecules in the crystalline lens of the eye through a light-receiving optical system to a photoelectric transducer, and by determining in accordance with the output signals of the photoelectric transducer.

The apparatus is provided not only a light optical system for emitting and converging a laser beam to an eye and for receiving the light beam scattered by molecules in the crystalline lens by this laser beam, but also a projection optical system for projecting fixation target to fix the eye gaze of the eye under examination on fixed direction and an illumination light system for illuminating anterior of the eye, and so on.

However, the light beam of fixation target and the light intensity of the illumination light beam of anterior of the eye are much more than the light intensity scattered by molecules in the crystalline lens.

The reflected light from the cornea or the like is transmitted to the light-receiving optical system for receiving the scattered light, and then causes the noise ingredient. It is an obstacle to achieve accurate results of measurements.

SUMMARY OF THE INVENTION

The present invention has been made in view of the above circumstances and has an object to overcome the above problems and to provide an ophthalmic measuring apparatus, which may eliminate the noise ingredient of the light without eliminating the light beam scattered by molecules in the crystalline lens of the examiner, to achieve stable and accurate results of measurements.

To achieve the objects and in accordance with the purpose of the present invention, as embodied and broadly described herein, an ophthalmic measuring apparatus of this invention comprises a laser beam irradiating optical system for emitting and converging a laser beam to an eye, a scattered light detecting optical system for detecting a light scattered by molecules in a crystalline lens by the laser beam, means for measuring a composition in the crystalline lens on the basis of the intensity of the light detected by the scattered light detecting optical system, and a first polarizing filter which is disposed in the scattered light detecting optical system so as to be consistent with the polarizing axis of the laser beam of the laser beam irradiating optical system.

The apparatus further comprises a fixation point projecting optical system for projecting a fixation target point into the fundus oculi of the eye, a third polarizing filter which is disposed in the fixation point projecting optical system, of which the polarizing axis is arranged in order that the light beam reflected by anterior of the eye and also transmitted to the scattered light detecting optical system is cut by the first polarizing filter.

The apparatus further comprises an illumination light system for illuminating anterior of the eye, a fourth polarizing filter of which the polarizing axis is disposed in the illumination light system so that the light beam reflected by anterior of the eye and also transmitted to the scattered light detecting optical system is cut by the first polarizing filter.

Another apparatus of this present invention comprises a laser beam irradiating optical system for emitting and converging a laser beam to an eye, a scattered light detecting optical system for detecting a light scattered by molecules in a crystalline lens by the laser beam, means for measuring a composition in the crystalline lens on the basis of the intensity of the light detected by the scattered light detecting optical system, a first polarizing filter which is disposed in the scattered light detecting optical system, and a second polarizing filter which is disposed in the laser beam irradiating optical system so as to be consistent with the polarizing axis of the first polarizing filter.

According to the present invention, it is capable of detecting the scattered light effectively.

Also, it is capable of eliminating the noise ingredient of the light reflected from the cornea and of detecting the only scattered laser beam which is to be measured. So it is capable of achieving stable and accurate results of measurements.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
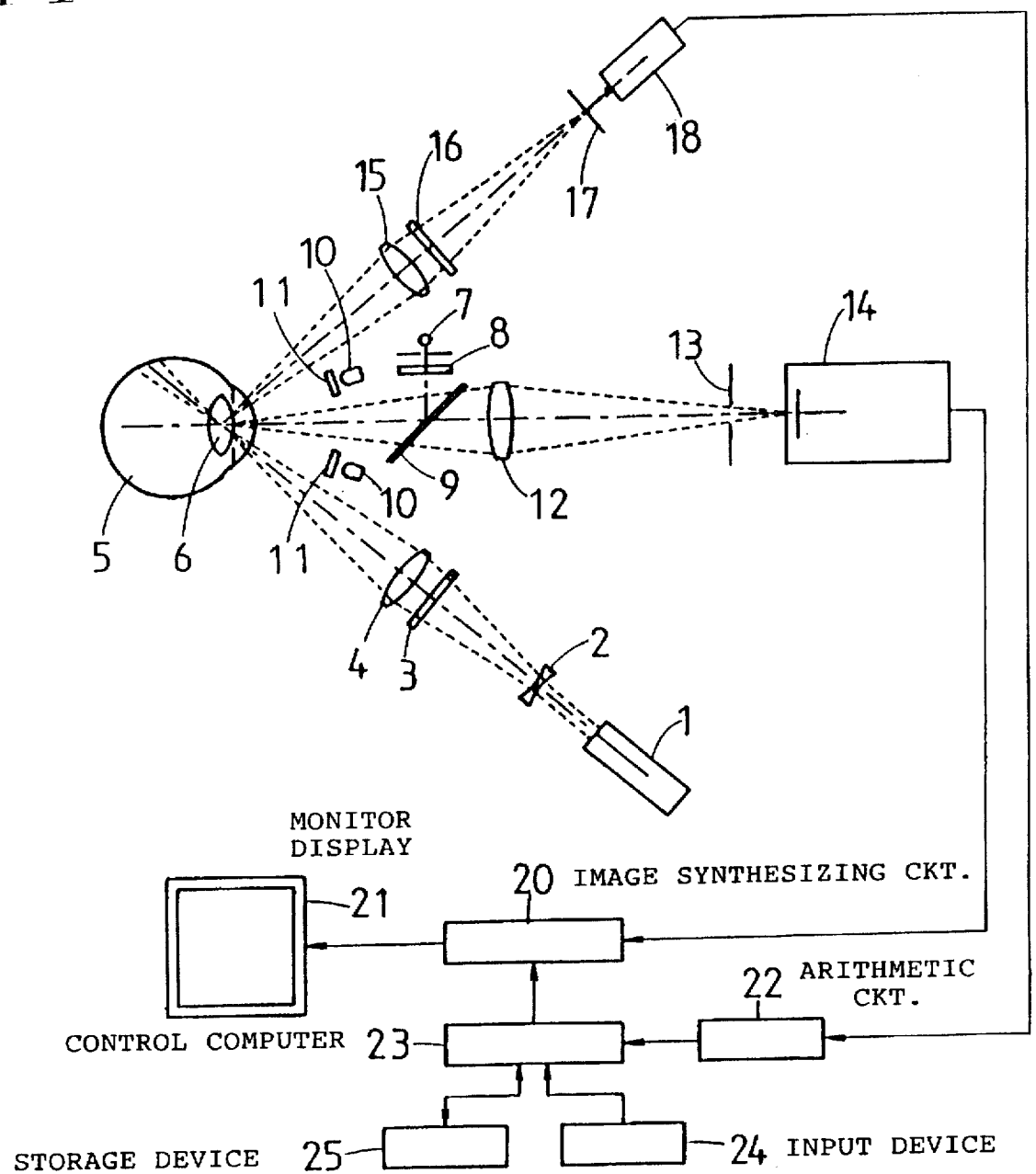
FIG. 1 is a schematic view showing the overview of an embodiment of an apparatus according to the present invention.

A detailed description of one preferred embodiment of an ophthalmic measuring apparatus embodying the present invention will now be given referring to the accompanying drawings.

In FIG. 1, there is shown the overview of a measuring apparatus of the first preferred embodiment according to the present invention for measuring protein composition within a crystalline lens, and an optical system is looked from the upper part.

In the drawings, reference numeral 1 designates a visible laser beam source for emitting an He—Ne visible laser beam, 2 is an expander lens, 3 is a polarizing filter. The polarizing filter 3 adjusts the polarizing axis of the laser beam to linear polarized light beam. If the laser beam from the visible laser beam source 1 has the polarizing axis and it can arrange the polarizing axis of the laser beam correctly, it can be omitted. Reference numeral 4 is a condenser lens. The above mentioned members 1 to 4 constitute a laser beam irradiating (projecting) optical system for measuring the protein composition within a crystalline lens. Reference numeral 5 designates an eye under examination, 6 is a crystalline lens.

Reference numeral 7 designates a point light source for fixation, and 8 designates a polarizing filter for fixation. The polarizing filter 8 is placed at right angles to the polarizing axis of the polarizing filter 3 on an eye under examination 5. Reference numeral 9 designates a beam splitter. The members 7 to 9 constitute a fixation point projection optical system for projecting a fixation target point into the fundus oculi of the eye.

Reference numeral 10 is an illuminating light source for illuminating the anterior of the eye, and 11 is a polarizing filter for an illuminating light sources. A polarizing axis of the polarizing filter 11 is placed at right angles to a polarizing axis of the polarizing filter 3 on an eye under examination 5. The members 10 and 11 constitute an illumination light system for illuminating the anterior of the eye.

The members 12 to 14 constitute an observation optical system for observing the anterior of the eye, 12 is an image forming lens, 13 is a diaphragm, and 14 is a CCD camera.

Reference numeral 15 is an image forming lens, and 16 is a polarizing filter placed in the detecting optical system. The polarizing axis of the polarizing filter 16 is arranged in order that the light reflected from the cornea of the fixation point projection optical system and the illumination light system may not pass through the polarizing filter 16.

Reference numeral 17 is an aperture, and 18 is a photoelectric transducer. The members 15 to 18 constitute a scattered light receiving (detecting) optical system.

Reference numeral 20 designates an image synthesizing circuit, 21 is a monitor display. Reference numeral 22 designates an arithmetic circuit, and it operates the fixed arithmetic operation in response to the output signals of the photoelectric transducer for measuring the condition of a crystalline lens. Reference numeral 23 is a control computer which controls all of the operations of the apparatus, 24 is an input device which has switches for operating the apparatus, and 25 is a storage device which memorizes the results of measurement.

The operation of the apparatus with the above mentioned configuration will now be described.

The examiner fixes the fixation target to the eye to be measured. The light beam of fixation target through the polarizing filter 8 from the point light source 7 for fixation lamp is reflected from beam splitter 9, and is transmitted to the eye under examination, and projects the figure of point light source 7 into the fundus oculi of the eye.

The examiner observes the image of the anterior portion of the eye displayed on the monitor display 21. The illumination light beam from the illumination light source 10 passed through the polarizing filter 11 is reflected on the anterior portion of the eye, and then it projects the image of the anterior of the eye on the image pick-up plane of the CCD camera 14 by passing through the image forming lens 12 and the diaphragm 13. And the laser beam output from the visible laser beam 1 is expanded its flux by an expander lens 2 and passed through the polarizing filter 3, and then converged by the condenser lens 4 from an oblique direction to the crystalline lens 6 of the eye. The laser beam scattered by molecules in the crystalline lens 6 under examination is taken by the CCD camera 14. The image taken by CCD camera 14 is observed with the monitor display 21. The examiner decides the site to measure, while operating a joy stick (not shown), and initiates a measurement by operating the input device 24 to generate a trigger signal.

The light beam transmitted to the eye under examination from the point light source 7 and the illuminating light source 10 is reflected from the cornea and so on, and the part of the light beam is transmitted to the scattered light detecting optical system. The polarizing axis of the polarizing filter 16 on its cornea is placed at right angles to the polarizing filter 8 in front of the point light source 7 and the polarizing filter 11 in front of the illuminating light source 10, so this light beam reflected from the cornea can not pass through the polarizing filter 16, and it is cut.

On the other hand, although the laser light beam scattered by particles of the protein in the crystalline lens 6 is also transmitted to the polarizing filter 16 in the scattered light detecting optical system, the laser light beam of which the polarizing components are the same as those of the polarizing filter 16 can pass through the polarizing filter 16. The scattered laser beam through the polarizing filter 16 passes through the aperture 17 restricting the measurement area, and then is transmitted to the photoelectric transducer 18. As described above, by being placed the polarizing filter 16 at right angles to the polarizing axis of the light beam projected on the eye under examination without the laser light beam, the photoelectric transducer 18 can detect only the scattered laser beam by particles of protein molecules in the crystalline lens 6.

The photoelectric transducer 18 outputs an electric signal corresponding to the intensity of the scattered light incident thereon, of which signal is transmitted to the arithmetic circuit 22. The arithmetic circuit 22 determines a correlation function of the fluctuation with time of the intensity of the scattered light. Based on this correlation function, the control computer 23, in turn, can derive the results on the protein composition in the crystalline lens. In the measurement, as described for example, in the Japanese Patent Laid-open No. Hei 6-505650 (PCT No. wo 92/11799) entitled as "Method of Detecting Cataract and Apparatus for Carrying out the Same," the correlation function of the fluctuation with in time of the intensity of the scattered light may be given by the following expression:

$$C(\tau) = \alpha (I_f e^{-\nu \tau} f + I_s \cdot e^{-\nu \tau} s)^2 + (I_f + I_s + I_{imm})^2$$

where:

$\tau f$: Constant relating to the size of not agglutinated particles $\tau s$: Constant relating to the size of agglutinated particles p1 If: Intensity of light scattered by not agglutinated particles Is: Intensity of light scattered by agglutinated particles Iimm: Intensity of light scattered by stationary particles $\alpha$: Constant specific to the optical system.

The protein composition of the crystalline lens is calculated from the ratio (quantity) between the intensity "If" of light scattered by not agglutinated particles and the intensity "Is" of light scattered by agglutinated particles.

The results of measurements is synthesized with the image output from the CCD camera 14 and it is displayed on the monitor display 21. The results of the measurement is memorized in the storage device 25.

The forgoing description of the preferred embodiments of the invention has been presented fop purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the present invention and its practical application to enable one skilled in the art to utilize the present invention in various embodiments and with various modifications as are suited to the particular use contemplated. It is intended that the scope of the present invention be defined by the claims appended hereto, and their equivalents.

What is claimed is:

1. An ophthalmic measuring apparatus comprising:

a laser beam irradiating optical system for emitting and focusing a laser beam having a polarizing axis to an eye a scattered light detecting optical system including a detector for detecting a light scattered by molecules in a crystalline lens of the eye by said laser beam;

measuring means for measuring a composition in the crystalline lens on the basis of the intensity of the light detected by said scattered light detecting optical system;

wherein a first polarizing filter is disposed in front of said detector in said scattered light detecting optical system that includes a polarizing axis that corresponds with the polarizing axis of the laser beam emitted from said laser beam irradiating optical system;

wherein the first polarizing filter passes the light scattered by the molecules in the crystalline lens by said laser beam to said detector and cuts noise light having a polarizing axis different than the polarizing axis of the first polarizing filter.

2. An ophthalmic measuring apparatus according to claim 1, further comprising:

a fixation point projecting optical system for projecting a fixation target point into the fundus oculi of the eye, wherein a second polarizing filter is disposed in said fixation point projecting optical system that includes a polarizing axis arranged in order so that the light beam reflected by an anterior of the eye and also transmitted to the scattered light detecting optical system as the noise light is cut by said first polarizing filter.

3. An ophthalmic measuring apparatus according to claim 2, further comprising:

an illumination light system for illuminating an anterior of the eye, wherein a third polarizing filter is disposed in said illumination light system that includes a polarizing axis arranged in order so that the light beam reflected by the anterior of the eye and also transmitted to the scattered light detecting optical system as the noise light is cut by said first polarizing filter.

4. An ophthalmic measuring apparatus according to claim 3, wherein the third polarizing filter has a polarizing axis at a right angle to the polarizing axis of the first polarizing filter.

5. An ophthalmic measuring apparatus according to claim 3, wherein the second polarizing filter and the third polarizing filter each have a polarizing axis at a right angle to the polarizing axis of the first polarizing filter.

6. An ophthalmic measuring apparatus according to claim 2, wherein the second polarizing filter has a polarizing axis at a right angle to the polarizing axis of the first polarizing filter.

7. An ophthalmic measuring apparatus comprising:

a laser beam irradiating optical system for emitting and focusing a laser beam having a polarizing axis to an eye;

a scattered light detecting optical system including a detector for detecting a light scattered by molecules in a crystalline lens of the eye by said laser beam; and measuring means for measuring a protein composition in the crystalline lens on the basis of the intensity of the light detected by said scattered light detecting optical system;

wherein a first polarizing filter is disposed in said scattered light detecting optical system;

wherein a second polarizing filter which is disposed in said laser beam irradiating optical system and includes a polarizing axis, which defines the polarizing axis of the laser beam, that corresponds with a polarizing axis of said first polarizing filter; and wherein the first polarizing filter passes the light scattered by the molecules in the crystalline lens by said laser beam to said detector and cuts noise light having a polarizing axis different than the polarizing axis of the first polarizing filter.

8. An ophthalmic measuring apparatus according to claim 7, further comprising:

a fixation point projecting optical system for projecting a fixation target point into the fundus oculi of the eye, wherein a third polarizing filter is disposed in said fixation point projecting optical system that includes a polarizing axis arranged in order so that the light beam reflected by an anterior of the eye and also transmitted to the scattered light detecting optical system as the noise light is cut by said first polarizing filter.

9. An ophthalmic measuring apparatus according to claim 8, further comprising:

an illumination light system for illuminating an anterior of the eye, wherein a fourth polarizing filter is disposed in said illumination light system that includes a polarizing axis arranged in order so that the light beam reflected by the anterior of the eye and also transmitted to the scattered light detecting optical system as the noise light is cut by said first polarizing filter.

10. An ophthalmic measuring apparatus according to claim 9, wherein the fourth polarizing filter has a polarizing axis at a right angle to the polarizing axis of the first polarizing filter.

11. An ophthalmic measuring apparatus according to claim 9, wherein the third polarizing filter and the fourth polarizing filter each have a polarizing axis at a right angle to the polarizing axis of the first polarizing filter.

12. An ophthalmic measuring apparatus according to claim 8, wherein the third polarizing filter has a polarizing axis at a right angle to the polarizing axis of the first polarizing filter.

* * * * *

UNITED STATES PATENT AND TRADEMARK OFFICE
CERTIFICATE OF CORRECTION

PATENT NO. : 5,726,735
DATED : March 10, 1998
INVENTOR(S) : Maunori KAWAMURA et al.

It is certified that error appears in the above-indentified patent and that said Letters Patent is hereby corrected as shown below:

IN THE TITLE: Item [54] and Column 1, line 1,

Insert --Ophthalmic-- before "Measurement"

Signed and Sealed this

Twenty-third Day of June, 1998

Attest:

BRUCE LEHMAN

*Attesting Officer*     *Commissioner of Patents and Trademarks*